United States Patent
Freitag et al.

[11] Patent Number: 5,480,431
[45] Date of Patent: Jan. 2, 1996

[54] TRACHEAL STENT

[75] Inventors: Lutz Freitag, Essen; Armin Singvogel, Remseck; Klaus Schmitt, Remshalden, all of Germany

[73] Assignee: Willy Rusch AG, Rommelshausen-Kernen, Germany

[21] Appl. No.: 185,984

[22] PCT Filed: Jul. 8, 1993

[86] PCT No.: PCT/DE92/00570

§ 371 Date: Jan. 10, 1994

§ 102(e) Date: Jan. 10, 1994

[87] PCT Pub. No.: WO93/00869

PCT Pub. Date: Jan. 21, 1993

[30] Foreign Application Priority Data

Jul. 11, 1991 [DE] Germany .................. 41 22 923.1

[51] Int. Cl.⁶ .................................................. A61F 2/04
[52] U.S. Cl. .......................... 623/9; 623/11; 623/12
[58] Field of Search ............................. 623/9, 11, 12, 623/1

[56] References Cited

U.S. PATENT DOCUMENTS

| | | | |
|---|---|---|---|
| 3,657,744 | 4/1972 | Ersek | 623/11 |
| 3,818,515 | 6/1974 | Neville | 623/9 |
| 4,728,328 | 3/1988 | Hughes et al. | |
| 4,795,465 | 1/1989 | Marten | |
| 5,019,040 | 5/1991 | Itaoka et al. | |
| 5,047,050 | 9/1991 | Arpesani | 623/12 |
| 5,171,262 | 12/1992 | MacGregor | 623/11 |
| 5,236,447 | 8/1993 | Kubo et al. | 623/12 |
| 5,258,027 | 11/1993 | Berghaus | 623/9 |
| 5,282,860 | 2/1994 | Matsuno et al. | 623/11 |
| 5,306,300 | 4/1994 | Berry | 623/11 |
| 5,336,256 | 8/1994 | Urry | 623/11 |
| 5,344,411 | 9/1994 | Domb et al. | 623/11 |
| 5,366,504 | 11/1994 | Anderson et al. | 623/11 |

FOREIGN PATENT DOCUMENTS

| | | |
|---|---|---|
| 0481365 | 4/1992 | European Pat. Off. . |
| 0587197 | 3/1994 | European Pat. Off. .............. 623/12 |
| 2617721 | 1/1989 | France . |
| 2667783 | 4/1992 | France . |
| 1541253 | 10/1969 | Germany . |
| 4032759 | 4/1992 | Germany . |
| 9201093 | 5/1992 | Germany . |
| 2189150 | 10/1987 | United Kingdom . |
| WO89/07916 | 9/1989 | WIPO . |

*Primary Examiner*—David H. Willse
*Assistant Examiner*—Bruce E. Snow
*Attorney, Agent, or Firm*—Thomas R. Vigil

[57] ABSTRACT

A tracheal stent 1 is comprised from a plastic shaft 2 and metal clasps 5 which grasp the plastic shaft 2 ventrolaterally. The plastic shaft 2 is, cranially, lengthwise oval in cross section and, caudally, squarish-oval. It is comprised from thin highly-elastic and stable sheet and from clasps 5, whereby the clasps 5 are bound to the sheet. The clasps 5 can, in a first manifestation, be sufficiently compressed together over their free ends 6, 7 that the plastic shaft 2 is given as small an outer circumference as possible. In a second manifestation, the clasps 5 can be spread out by, for example, being heat activated. A stably-shaped and, in section 7', highly-elastic lumen 8 is formed in plastic shaft 2 which largely corresponds to the size of a lumen of a natural trachea.

10 Claims, 1 Drawing Sheet

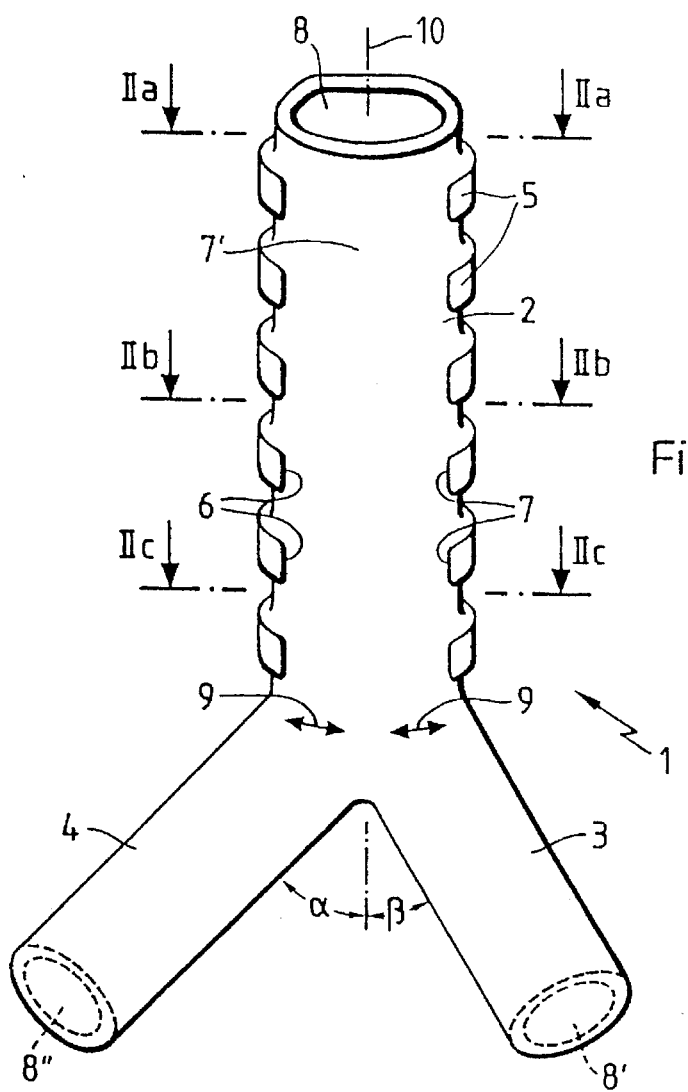
Fig. 1
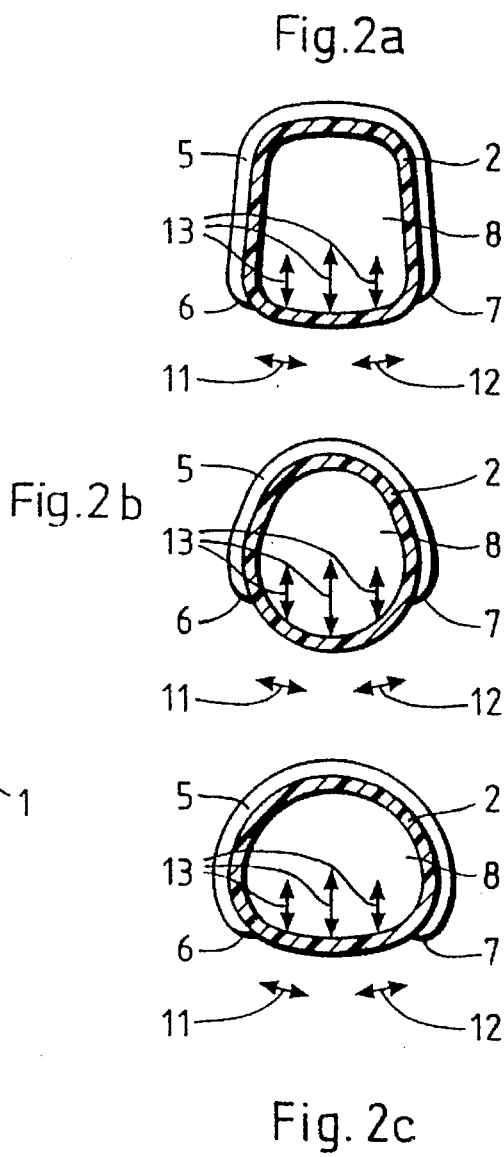
Fig. 2a
Fig. 2b
Fig. 2c

TRACHEAL STENT

BACKGROUND OF THE INVENTION

The invention concerns a tracheal stent for constricted diseased tracheal and/or bronchial sections made out of a plastic shaft.

Furthermore, a tracheal stent is known in the art from U.S. Pat. No. 4,728,328 which is configured in a pipe-shaped fashion and is surrounded by a support spiral. The spiral is coated and wound around the pipe-shaped stent.

A tracheal stent of this kind has become known in the art through U.S. Pat. No. 4,795,465.

The known tracheal stent is comprised from a tracheal arm which splits on one end into two bronchial arms. The tracheal arm as well as the bronchial arms are manufactured from a tube-shaped plastic which is stiff over its entire axial length and forms a stable lumen.

Tracheal stents are normally used when medical application of an artificial tracheal prosthesis is no longer possible or too dangerous. Terminal tumor patients can, by means of suitable palliative measures, have the inner volume of their tracheas kept open for the purposes of breathing in that, by means of an endoscope, inserts or pipe-like stents are introduced into the constricted air pipe. The stents which have been used up to this time exhibit, however, significant disadvantages and insufficiencies in view of the purpose of their use, and with regard to their outer shape, the low mechanical strength of the stent walls, as well as with regard to mucous transport of the natural mucous clearance.

The underlying purpose of the invention is therefore to further improve the known tracheal stent in such a fashion that in can be endoscopically applied without any problems, in that it exhibits sufficient resistance to the pressure from tumors or scars and in that it can adapt to rapid pressure changes in the event of coughing. The seating of the known tracheal stent in the natural trachea is to be improved in such a fashion that it seats with as little pressure as possible on the mucous membrane.

SUMMARY OF THE INVENTION

This purpose is achieved in accordance with the invention in that the plastic shaft exhibits means which, in a first manifestation, reduce the outer circumference of the plastic shaft and, in a second manifestation, widen the plastic shaft over the entire axial length to form a lumen along an axis in the plastic shaft, the lumen exhibiting a crosssectional shape of a natural trachea, whereby the plastic shaft is rigid in the ventrolateral region and is highly elastic in the dorsal region.

The tracheal stent in accordance with the invention thereby has the significant advantage that it is capable of exhibiting complicated strongly contrasting plastic elastic properties. It can be situated without problems by means of a tube, and can, with special means, withstand the pressure of tumors in that these means exhibit a buttressing effect with it furthermore being possible for the inventive tracheal stent to adapt to pressure fluctuations during coughing.

The means are, for example, metal clasps made from memory metal which seat on the exterior of the plastic shaft and which, in the ventrolateral region of the plastic shaft, highly stabilize or stiffen the shaft and in the dorsal region allow the plastic shaft to exhibit a high elasticity. This is, for example, possible in that the plastic shaft is made from a silicon material. A principal problem in long-term applications, namely mucous congestion, can in this fashion be successfully counteracted. For a drop of mucous, the gravitational attraction is proportional to the square of the gas-flow velocity. If one of the known stents is introduced into the tumor stenosis in order to widen the lumen, the flow velocity is locally reduced to a minimum here since the surface to be streamed through becomes too large and secretions collect in the stent. With the tracheal stent in accordance with the invention it is possible to achieve high gas-flow velocities in that, in the event of coughing, the cross-sectional area in the highly-elastic dorsal region is reduced. The inventive tracheal stent can dynamically propagate the coughing force. Dynamical properties of real air pipes or bronchial tubes are therefore imitated to as good an extent as possible. The highly elastic dorsal portion of the plastic shaft behaves like a flexible membrane and the cleaning of secretions is therefore significantly improved.

The tracheal stent in accordance with the invention is easily introduced by means of an endoscope into the trachea. A stenosis which needs to be passed is, if necessary, done so with a bougie and, subsequentially, the compressed or collapsed plastic shaft is inserted into the trachea. Finally the means on the plastic shaft are activated in such a fashion that the plastic shaft unfolds and assumes a permanent shape which guarantees that a lumen of sufficient size is maintained.

If the means comprise metal clasps with a memory effect (shape-memory alloy), then this has the advantage that they, subject to a temperature treatment, can assume a predetermined cross-sectional shape and can, as viewed in the axial direction, widen the natural trachea to differing degrees.

The metal clasps are integral with the plastic, which is a sheet exhibiting a wall thickness between 0.4 mm and 1.5 mm. In the widened state of the plastic shaft it is thereby possible to largely imitate a natural trachea. In the trachea stent in accordance with the invention, the clasps and the sheet form a composite material which corresponds to the known plastic shaft and replaces it. The clasps thereby form a reliable and stable buttress against the natural trachea-narrowing tumor.

The metal clasps are open and in cross section, viewed cranially, form a horse-shoe shape and in the collapsed state the clasp ends can overlap or can abut each other. When the metal clasps are opened, the distinct free ends of these clasps become separated from another. Should the clasps be opened wide under the action of thermal effects, the warmth can be introduced via the endoscope after placement of the folded-together tracheal stent. The widening of the clasps can also be done using body heat.

The clasps exhibit different cross sections along the length of the stent so that in the widened state, they simulate as closely as possible the natural tracheal cartilage rings at the corresponding positions.

Should the clasps be slightly more strongly widened than the given lumen size of the natural trachea, the stent seats and cannot be dislodged. The stent is caudally elongated and oval and cranially squarish-oval, whereby in the middle a nearly oval cross section is achieved. This guarantees an optimal seating with as little pressure as possible on the mucous membrane. Sufficient capillary circulation is guaranteed—an important requirement for sufficient dynamic flow and the necessary mucous clearance.

Arranging the metal clasps on the outer circumference of the plastic shaft has the advantage that the inner surface of the lumen of the plastic shaft is, in addition, easy to hydrophilate. By means of this measure the function of the fibrilating cilia is simulated.

The clasps can be completely surrounded by the sheet which together with the clasps form the plastic shaft so that clasp material can also be utilized which is not particularly compatible with tissue but which develops particularly advantageous and long-lasting restoring forces which are necessary to maintain the required lumen size.

Expanding plastic materials, which exhibit no metal components, can also be utilized as clasps. If the sheet of the plastic shaft is temperature insensitive, the clasps can be enlarged from small outer diameters to clasps with a larger outer diameter through the introduction of heat.

The clasps, separate from each other, are joined to each other via the sheet which, together with the clasps, form the inventive plastic shaft. It is thereby possible to arbitrarily shorten a standard prosthesis and to adjust it according to need. The inventive stent can be cut to size by the physician according to need. An extensive stocking of different stent sizes is therefore obviated.

Should the inventive tracheal stent be equipped with bronchial arms, the bifurcation exhibits two different angles with respect to the axis of the central plastic shaft. In this fashion the stent can be adjusted to the natural shape of the bronchial sections to as good an extent as possible and without pressure. It is therefore preferred to always manufacture the tracheal stent as a Y-Stent and the physician can shorten it at arbitrary locations according to need.

Embodiments of the invention provide for the clasps to be formed only in the tracheal portion of the stent and not in the bronchial arms. In addition, clasps can also be utilized whose free clasp ends abut against each other in the folded-together state. In the expanded state of the plastic shaft the free ends of these clasps are separated from each other to a greater or lesser extent. If no clasps are provided for on the bronchial arms of the stent, these sections can be fashioned from a plastic sheet with a shape which is more stable than that of the plastic sheet utilized for the tracheal section.

Further advantages can be derived from the description and the accompanying drawing. Likewise the above-mentioned features and those to be described below in accordance with the invention can be utilized individually or collectively in arbitrary mutual combination. The embodiments mentioned are not to be taken as exhaustive enumeration, rather have only exemplary character.

The invention is shown in the drawing and is described more closely with regard to the embodiments.

BRIEF DESCRIPTION OF THE DRAWINGS

FIG. 1 shows a tracheal stent in accordance with the invention with a tracheal portion and both bronchial arms;

FIG. 2a a cut IIa—IIa of FIG. 1;

FIG. 2b a cut IIb—IIb of FIG. 1;

FIG. 2c a cut IIc—IIc of FIG. 1.

The objects in the figures are partially shown in a highly schematic fashion and show the objects not to scale. Furthermore the objects are partially shown in a highly expanded fashion so that their construction can be better illustrated.

DESCRIPTION OF THE PREFERRED EMBODIMENT

FIG. 1 shows a widened or opened tracheal stent 1 with a first plastic shaft 2, a second plastic shaft 3 and a third plastic shaft 4 as it can be inserted into a natural trachea to splint same. The first plastic shaft 2 corresponds to the tracheal portion of the stent and the second, and third plastic shafts 3, 4 correspond to the bronchial tubes.

In the figure, the first plastic shaft 2 is grasped by clasps 5. The clasps 5 form an integral material composite with the first plastic shaft 2. The first plastic shaft 2 is manufactured from a plastic sheet which is largely neutral with respect to tissue. The thickness of the sheet material is between 0.4 mm and 1.5 mm.

The clasps 5 are, in one embodiment, manufactured from metal which exhibits, in a known fashion, memory properties. In another embodiment of the invention the clasps 5 are manufactured from a plastic material which, in a first state, is flexible and shapeable and, in a second state, exhibits a stable shape and is porous.

Clasps 5 are provided, in FIG. 1, with free ends 6, 7 which are separated from another. The clasps 5 themselves are separated from each other in the axial direction of the first plastic shaft 2 and are only connected to each other by means of the plastic material (sheet) of the plastic shaft 2. The clasps 5 provide the first plastic shaft 2 with a stable shape and hold open a lumen 8 in the plastic shaft 2. The clasps 5 grasp the first plastic shaft 2, in the widened state, ventrolaterally only and dorsally border, with their free ends 6, 7, a highly-elastic section 7' of the plastic shaft 2.

The clasps 5 can be moved in the direction of the arrows 9 to such an extent that the free ends 6, 7 overlap or at least abut. If the free ends 6, 7 are directed towards another, it is thereby possible for the plastic shaft 2 to be introduced into a small outer opening. The clasps 5, during application, are pressed together to such an extent that they fit into the lumen of a known endoscope and can be introduced through same.

The second plastic shaft 3 and the third plastic shaft 4 are, in the embodiment of FIG. 1, manufactured from an unreinforced plastic sheet, which, when unfolded, maintains its unfolded shape to define a lumen 8', 8". The second and third plastic shafts 3, 4 are each angled with respect to an axis 10 at an angle α, which preferentially assumes a value of 36.3°, and an angle β which preferentially is 46.3°. The plastic shafts 3, 4 corresponding to the bronchial tubes can be compressed together so that they can be introduced through the rima glotidis. The unfolding of the plastic shafts 3, 4 transpires, under observation, through the tracheal tube preferentially with the assistance of a large gripping and spreading forceps.

The extremely simplified tracheal stent represented in FIG. 1 can exhibit, along the axis 10, different cross-sectional shapes which, for example, are represented in FIGS. 2a, 2b, 2c.

FIG. 2a shows, cranially, a section in the direction of arrow IIa—IIa of FIG. 1. The first plastic shaft 2 of the tracheal stent is ventrolaterally surrounded by the clasp 5, which holds the sheet of the first plastic shaft 2 in a stable shape for maintaining the lumen 8. The stent exhibits, in this region, a lengthened oval shape. The clasp 5 is shown with separated free ends 6, 7. Should the clasp 5 be compressed in the direction of arrows 11, 12, the outer diameter of the tracheal stent can be, to this extent, reduced. Should the clasps 5 be manipulated so their free ends overlap or should the free ends 6 and 7 abut, the clasps 5 exhibit either a restoring force which allows for the clasps 5 to spontaneously open to a shape shown in FIG. 2a or, the clasp 5 is, for example, activated by the incluence of heat so that it unfolds into the shape shown in FIG. 2a. In the figure, the free ends 6 and 7 taper towards the end.

The highly-elastic section 7' can accept rapid pressure changes and propagate them in a wave-like fashion. In this manner, the section 7' can reduce the cross section of the lumen in the direction of the arrow 13 in a pulse-like fashion and thereby suddenly increase the gas-flow velocity.

In contrast to FIG. 2a, FIGS. 2b and 2c exhibit different cross-sectional shapes of the clasps 5 in the expanded state in the middle and caudal regions respectively. With this type of configuration of the clasps 5 it is possible to effect different lumen cross sections along the axis 10 (FIG. 1).

FIG. 1 and FIG. 2 show the inventive tracheal stent 1 in the expanded state. In the state shown, it maintains the respiratory path of a natural trachea open in the direction of the bronchia.

Clearly, the second and third plastic shafts 3, 4 (FIG. 1) can also be encased by clasps 5. These clasps 5 can also be pressed together and open again in the manner already described.

A tracheal stent 1 is comprised from a plastic shaft 2 and metal clasps 5 which grip the plastic shaft 2 ventrolaterally. The plastic shaft 2 is, caudally, lengthwise oval in cross section and, cranially, squarish-oval. It is comprised from thin, highly-elastic and stable sheet and from clasps 5, whereby the clasps are joined to the sheet. The clasps 5, in a first shape, can be sufficiently pressed together over their free ends 6, 7 such that the plastic shaft 2 assumes as small an outer circumference as possible. In a second shape, the clasps 5 are widened in that they, for example, are activated by heat. A stably-shaped and, in a section 7', highly-elastic lumen 8 are formed in the plastic shaft 2, the lumen largely corresponding to the size of a lumen of a natural trachea.

We claim:

1. A tracheal stent for narrowed, diseased trachea and bronchial sections comprising an elastic plastic shaft having an axis and an axial length, and resilient means integral with the shaft which, in a first state, reduce the outer circumference of the plastic shaft for insertion into the diseased section and, in a second state, expand the plastic shaft over the entire axial length to form a lumen along the axis for supporting and opening the diseased section, the lumen exhibiting a changing cross section which is squarish-oval in a cranial region, oval in a middle region and lengthened-oval in a caudal region to emulate a shape of a natural trachea.

2. The tracheal stent of claim 1, wherein the means comprise movable clasps, made from at least one of metal and plastic, which seat in an outer circumference of the plastic shaft.

3. The tracheal stent of claim 1, wherein an inner surface of the plastic shaft is hydrophilated.

4. The tracheal stent of claim 1, wherein an end of the plastic shaft branches into two arms to form additional plastic shafts.

5. The tracheal stent of claim 1, wherein the means comprise flexible clasps made from at least one of metal and plastic which are integral with the plastic shaft.

6. A tracheal stent for narrowed, diseased trachea and bronchial sections comprising an elastic plastic shaft having an axis and an axial length and resilient means integral with the shaft which, in a first state, reduce the outer circumference of the plastic shaft for insertion into the diseased section and, in a second state, expand the plastic shaft over the entire axial length to form a lumen along the axis for supporting and opening the diseased section, the lumen exhibiting a changing cross section which is squarish-oval in a cranial region, oval in a middle region and lengthened-oval in a caudal region to emulate a shape of a natural trachea, the resilient means being adapted to stiffen the plastic shaft in a ventrolateral region, the plastic shaft being highly elastic in a dorsal region.

7. The tracheal stent of claim 6, wherein the means comprise movable clasps, made from at least one of metal and plastic, which seat in an outer circumference of the plastic shaft.

8. The tracheal stent of claim 6, wherein an inner surface of the plastic shaft is hydrophilated.

9. The tracheal stent of claim 6, wherein an end of the plastic shaft branches into two arms to form additional plastic shafts.

10. The tracheal stent of claim 6, wherein the means comprise flexible clasps made from at least one of metal and plastic and which are integral with the plastic shaft.

* * * * *

UNITED STATES PATENT AND TRADEMARK OFFICE
CERTIFICATE OF CORRECTION

PATENT NO.    : 5,480,431
DATED         : January 2, 1996
INVENTOR(S)   : Lutz Freitag, Armin Singvogel and Klaus Schmitt It is certified that error appears in the above-identified patent and that said Letters Patent is hereby corrected as shown below:

Title page,
Item [22], PCT Filed, "July 8, 1993" should be -- July 8, 1992 --.

Signed and Sealed this

Seventh Day of March, 2006

JON W. DUDAS
*Director of the United States Patent and Trademark Office*